United States Patent [19]

Mundell et al.

[11] Patent Number: 4,700,697

[45] Date of Patent: Oct. 20, 1987

[54] CERVICAL APPLIANCE TO AMELIORATE SLEEP APNEAS

[76] Inventors: Robert D. Mundell, 542 Lucia Dr., Pittsburgh, Pa. 15221; C. Richard Bennett, 15 Forest Glen Dr., Pittsburgh, Pa. 15228

[21] Appl. No.: 732,281

[22] Filed: May 9, 1985

[51] Int. Cl.⁴ .................. A61H 31/00; A61F 5/01; A61F 5/37; A61F 5/04

[52] U.S. Cl. ..................... 128/75; 128/DIG. 23; 128/76 R; 128/87 B

[58] Field of Search ............. 128/DIG. 23, DIG. 20, 128/75, 76 R, 87 B

[56] References Cited

U.S. PATENT DOCUMENTS

| | | | |
|---|---|---|---|
| 3,075,521 | 1/1963 | Grassl | 128/DIG. 23 |
| 3,220,406 | 11/1965 | Connelly | 128/DIG. 23 |
| 3,530,853 | 9/1970 | Bond | 128/87 B |
| 3,696,810 | 10/1972 | Gaylord, Jr. | 128/DIG. 23 |
| 3,756,226 | 9/1973 | Calabrese et al. | 128/DIG. 23 |
| 4,099,523 | 7/1978 | Lowrey | 128/DIG. 23 |
| 4,325,363 | 4/1982 | Berkeley | 128/DIG. 23 |

FOREIGN PATENT DOCUMENTS 1544874  4/1979  United Kingdom ............... 128/75

Primary Examiner—Edgar S. Burr
Assistant Examiner—Tonya Lamb
Attorney, Agent, or Firm—Clifford A. Poff; Thomas H. Murray

[57] ABSTRACT

A cervical appliance for preventing ventral flexion of the head to reduce the possibility of sudden infant death syndrome and/or adult sleep apnea, both of which have common characteristics which are at least partially obviated with the use of the invention.

6 Claims, 9 Drawing Figures

CERVICAL APPLIANCE TO AMELIORATE SLEEP APNEAS

BACKGROUND OF THE INVENTION

A variety of theories have been proposed to explain sudden infant death syndrome (SIDS). SIDS is defined as "the sudden death of an infant or young child which is unexpectd by history, and in which a thorough post-mortem examination fails to reveal an adequate cause for death". While SIDS may occur for different reasons, one attribute of this phenomenon, included in the great majority of the cases described in the literature, is apnea (or respiratoray pause or periodic breathing) which occurs during sleep and is fatal. The autopsy reports describe conditions that are consistent with a condition of hypoxia and/or hypoxemia having existed for some time prior to the fatal apneic episode. It is the apneic character of SIDS which is addressed when "SIDS-risks" infants are placed on a cardiopulmonary monitor or treated with respiratory stimulants.

Some adult humans also suffer severe apnea during sleep (adult sleep apnea, or hypersomnia with periodic apnea [HPA]). SIDS and HPA share the fact that they occur during sleep, and that at least part of the apnea occurs without the subject's making any attempt to breathe. This latter condition is called "central apnea" because it appears to be ordered by the central nervous system. HPA oocurs most frequently in overweight males, over 40 years of age, who are given to strident or stentorian snoring. Typically, their obesity causes such individuals to sleep in a supine position. Careful observations have shown that they possess redundancy of tissue in the soft palate and the walls of the oropharynx. Part of this may be due to fatty deposit; part may be due to anatomical variation.

During sleep, especially "quiet sleep" or "REM (rapid eye-movement) sleep", facial muscles become hypotonic. During the inspiratory phase of the respiratory cycle the walls of the oropharynx and the base of the tongue tend to collapse onto the oropharynx. This is partly due to muscular hypotonia, partly due to negative pressure. The latter may be caused by negative intrathoracic pressure as air is breathed in, or by the Bernoulli effect (in which rapid airflow through a restricted space decreases the pressure).

It is the collapse of tissues into the oropharynx which produces central apnea. This occurs as the result of physical stimulation of the oropharyngeal wall, initiating a swallowing reflex during which respiration is suppressed. Occlusion of the oropharynx also causes an obstructive type of apnea, in which respiratory efforts are made against a blocked airway. Finally, mixed apneas occur in which an initial central phase is followed by an obstructive phase. Here the reflex cessation of breathing occurs, and when low oxygen and high carbon dioxide levels in the blood override the central apnea, the subject attempts to recommence breathing, but total obstruction has occured. If apneas are to be minimized in SIDS-risk infants or in adults with HPA, this encroachment on the oropharynx must be minimized.

When the head is flexed dorsally the cervical vertebrae and the cranial base are both moved away from the base of the tongue, whose upward and backward movement is prevented by its attchment through the strap muscles of the neck to the top of the sternum. Since the posterior pharyngeal wall is attched to the base of the cranium and the cervical vertebrae, dorsal head flexion increases space within the oropharynx. A device capable of maintaining slight dorsal flexion of the head during sleep, therefore, has the effect of ameliorating sleep apneas, whether in infants or adults.

SUMMARY OF THE INVENTION

In accordance with the present invention, an appliance for treatment of conditions of apneic SIDS and HPA is provided which involves a device fitted around the neck, and with adaptations specifically suited to maintaining the head in a slightly dorsally flexed position during sleep. Since the oropharyngeal airway is compromised by ventral head flexion and ameliorated by dorsal head flexion, this precaution will help to maintain an adequate separation between the oropharyngeal walls, the base of the tongue and related structures. In so doing, the appliance of the invention will minimize the conditions which relate to both central and obstructive apneas.

Specifically, the appliance of the invention comprises a foam rubber or plastic core and a soft cloth cover. The foam rubber core is compliant enough to be worn with comfort but firm enough to provide some support. The cloth cover keeps the foam away from the user's skin and also provides a means for attaching a mechanism for closure of the appliance. Additional support can be provided by a semirigid insert interposed anteriorly between the chin and the upper chest/clavicle region. This insert permits some adjustment in height to allow custom fitting of the device.

The specific function served by the appliance is maintenance of a slightly dorsally flexed position of the head, and prevention of ventral flexion of the head (i.e., bending toward the chest) during sleep. Since this favorable position decreases the occurrence of encroachment into the oropharynx by its own walls, by the soft palate and by the base of the tongue, it decreases the frequency and/or duration of apneic episodes during sleep.

While cervical prior-art appliances exist, they differ from the invention in design, structure and purpose. Prior-art appliances of this type may be fabricated of foam rubber, plastic or metal, and may be covered with cloth or otherwise padded for comfort. They are designed, however, to discourage flexion of the head in any direction and are intended to stabilize the head following neck injury. In addition, they permit any downward force of the chin, created when ventral head flexion is attempted, to be transmitted by the appliance and directed against the lower anterior part of the neck (a highly undersirable situation when airway obstruction is a concern, and particularly so in an infant whose tissues are especially compliant).

The above and other features of the invention will become apparent from the following detailed description taken in connection with the accompanying drawings which form a part of this specification, and in which.

Figure 1:
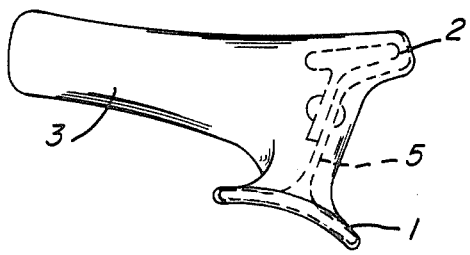
FIG. 1 is a lateral perspective view of the appliance of the invention shown in a closed position.
Figure 2:
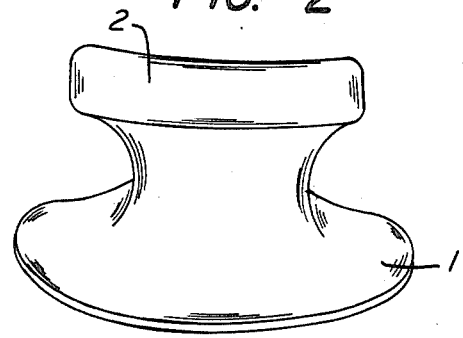
FIG. 2 is a frontal perspective view showing a chin cup, a scutum, and an interposed supporting portion.
Figure 3:
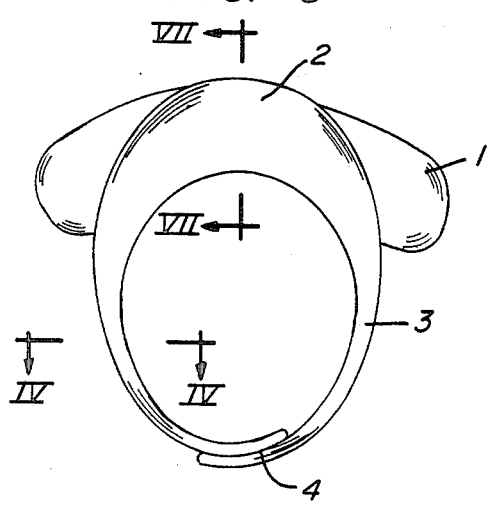
FIG. 3 is a superior perspective view showing the scutum, the chin cup, the lateral tabs, and the ends of the tabs which, fitted with adhesive surfaces, provide the closure mechanism for the appliance of the invention.
Figure 4:
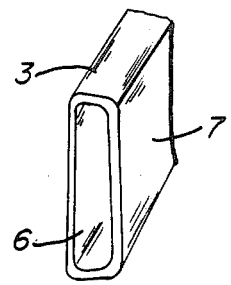
FIG. 4 is a section taken substantially along line IV—IV of FIG. 3 and shows the foam-rubber core of the appliance of the invention and its cloth cover.
Figure 5A:
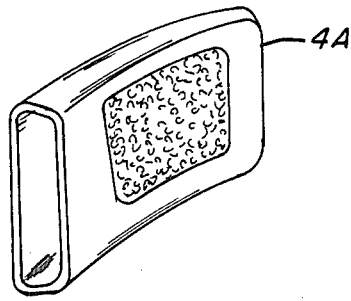
FIG. 5 is a view of the ends of the lateral tabs of the appliance and their integral attachment surfaces.
Figure 5B:
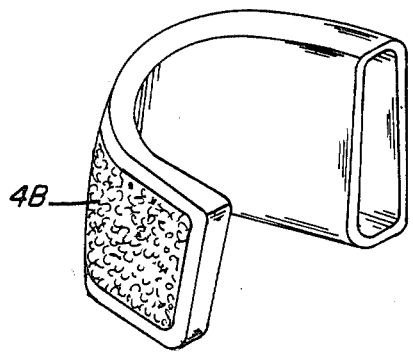
Figure 6:
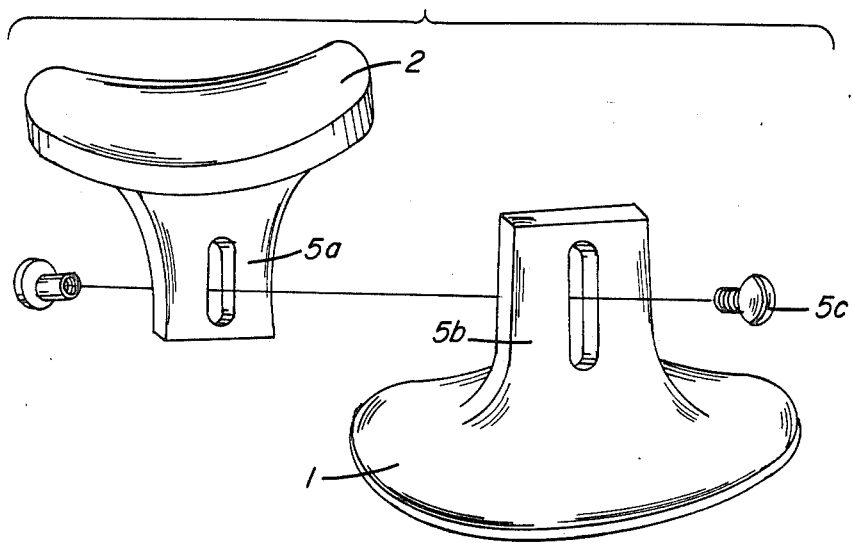
FIG. 6 is a perspective view of the upper and lower parts of a semi-rigid insert which helps to support the anterior portion of the appliance of the invention.
Figure 8:
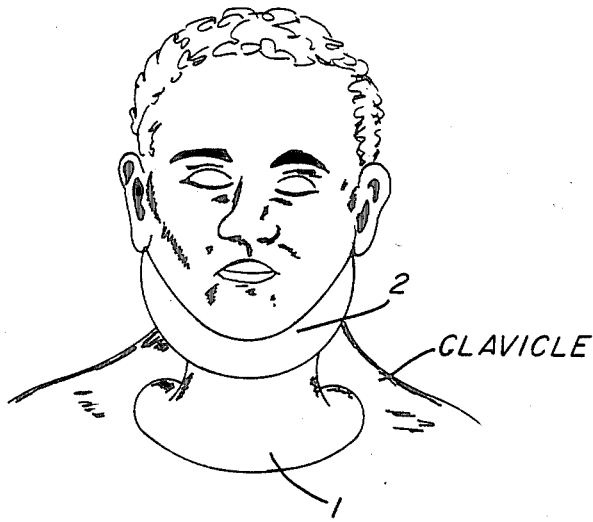
FIG. 8 is a frontal perspective view, showing the appliance of the invention as it is worn by an adult.
Figure 7:
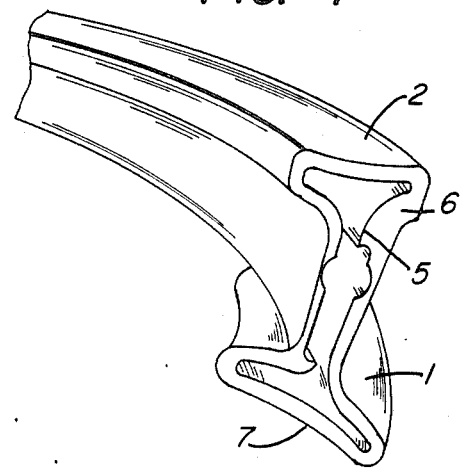
FIG. 7 is a section through the appliance taken substantially along line VII-VII of FIG. 3 and showing a sectioned view of the appliance and its supporting insert.
Figure 9:
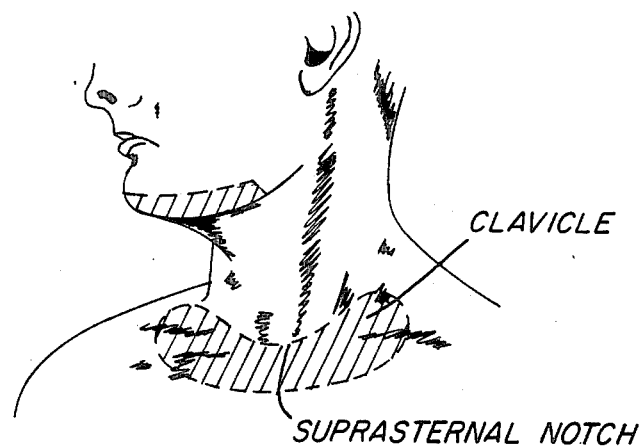
FIG. 9 is an illustration of the area of the chin and the area of the upper chest and clavicle region which serve as the principal load-bearing regions against which the appliance of the invention bears during use.

Referring now to the drawings, the appliance of the invention consists of an anterior portion which includes a chin cup 2 and scutum 1 separated by a support pillar within which is an adjustable semi-rigid support 5 (FIGS. 1 and 6). Extending backwardly from the interior portion of the appliance are lateral tabs 3 that are drawn backwardly around the neck to be fastened at their free ends 4A and 4B (FIG. 5). The shield-like scutum 1 rests on the medial portions of the clavicles and on the superior part of the sternum, accepting downwardly directed forces as shown in FIG. 8. The wearer's chin rests upon the chin cup 2. Cross-hatched portions shown in FIG. 9 comprise the optimal areas for force bearing on the chin and on the clavicle and upper-chest region of the user. The semi-rigid adjustable insert 5 provides both support and a means for increasing or decreasing the vertical height of the appliance in the anterior region. The insert 5 is covered with both foam-rubber core material 6 and a cloth surface-covering material 7. The core material 6 and the cloth material 7 extend backwardly along the lateral tabs 3 as shown in FIG. 4 and 5.

The tabs 3 and their closure 4 at the nape of the neck maintain the anterior support portion of the appliance in place and prevent it from moving downwardly and forwardly, which position would make the support portion ineffective by moving it from between the chin and the clavicle/sternum region. As shown in FIG. 5, the closure 4 may take the form of VELCRO (TM) patches 4A and 4B.

Force necessary to maintain the head in a slightly dorsally flexed position during sleep is applied against the inferior border of the chin by the chin cup 2. The amount of this force is determined by the vertical height of the anterior support portion of the appliance, this being adjusted by positioning the upper and lower components of the semi-rigid internal support formed of two parts 5a and 5b (FIG 6) and maintaining their positions by tightening screw rivet 5c. Any suitable means to access screw rivet 5c well known per se in the art may be provided. The buttress against which this force is applied by the scutum 1 is the clavicular and upper sternal region.

When the appliance is in use, its anterior height is adjusted to produce slight dorsal flexion of the wearer's head, sufficient to increase the oropharyngeal airway and minimize the tendency to apnea which oropharyngeal obstruction would produce. The wearer's chin is placed into the chin cup 2, the scutum 1 is placed simultaneously upon the clavicle/sternum area, and the lateral tabs 3 are drawn backwardly around the sides of the neck. When tension has been placed on the lateral tabs 3 sufficient to maintain the anterior support portion of the appliance in its place, the ends of the tabs 4A are closed against each other to maintain this fit.

The semi-rigid insert in the anterior portion of the appliance prevents collapse downward or inward of the appliance. Downward collapse would permit ventral head flexion, the thing the appliance is designed to prevent; inward collapse would permit impingement of the appliance on the larnyx or trachea, an undesirable situation.

Although the invention has been shown in connection with a certain specific embodiment, it will be readily apparent to those skilled in the art that various changes in form and arrangement of parts may be made to suit requirements without departing from the spirit and scope of the invention.

We claim as our invention:

1. A cervical appliance for maintaining slight dorsal flexion of the head during sleep, and for preventing ventral flexion, consisting of an anterior support column with a chin cup and a scutum, a internal support interconnecting said chin cup and scutum within the support column for supporting the head against ventral flexion, and means for securing said cervical appliance to a body without restraining dorsal or lateral flexion of the head, said securing means consisting of lateral tabs each havinag one end connected to said cervical appliance and extending backwardly around the neck of the user to a free end, each free end carrying means to secure said free ends together such that the sole function of said tabs is to retain said cervical appliance in place at the proper position.

2. The appliance of claim 1 wherein the appliance is formed of a pliable material covered with a cloth sheath.

3. The appliance of claim 2 wherein the appliance is formed from foam rubber.

4. The appliance of claim 1 wherein said internal support incorporates a generally straight vertical portion extending along the neck of the user and includes means for adjusting the vertical height of said chin cup into which the user's chin is fitted at an upper end of said support, above said scutum and said scutum at a lower end of said support being positioned at an outwardly-extending angle to rest on the upper chest and clavicle region of the user.

5. The appliance of claim 1 wherein the collar is split at the portion thereof which abuts against the back of the neck of the user, and fastener means for securing together the opposite sides of said split portion.

6. The appliance of claim 1 wherein said two laterial tabs have the same general construction as the anterior support column, and each tab tappering to a reduced thickness and reduced height along the length thereof said lateral tabs extending backwardly across the lateral sides of the root of the neck and having adjustable closure members for interconnecting said free ends of the tabs at the back of the neck.

* * * * *